US011331477B2

(12) United States Patent
Boor et al.

(10) Patent No.: US 11,331,477 B2
(45) Date of Patent: May 17, 2022

(54) NEUROSTIMULATION METHOD AND SYSTEM WITH CURRENT REGULATOR BIASED BY FLOATING POWER SUPPLY

(71) Applicant: ADVANCED NEUROMODULATION SYSTEMS, INC., Plano, TX (US)

(72) Inventors: Steven Boor, Plano, TX (US); Daran DeShazo, Lewisville, TX (US); Gavin L. Rade, Dallas, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 69 days.

(21) Appl. No.: 16/401,971

(22) Filed: May 2, 2019

(65) Prior Publication Data

US 2020/0346005 A1 Nov. 5, 2020

(51) Int. Cl.
*A61N 1/08* (2006.01)
*H02M 3/07* (2006.01)
*A61N 1/36* (2006.01)
*H02M 1/44* (2007.01)

(52) U.S. Cl.
CPC ......... *A61N 1/086* (2017.08); *A61N 1/36125* (2013.01); *A61N 1/36157* (2013.01); *H02M 1/44* (2013.01); *H02M 3/07* (2013.01)

(58) Field of Classification Search
CPC . A61N 1/086; A61N 1/36125; A61N 1/36157
See application file for complete search history.

(56) References Cited

U.S. PATENT DOCUMENTS

| 6,609,031 | B1 | 8/2003 | Law et al. |
| 7,180,760 | B2 | 2/2007 | Varrichio et al. |
| 7,212,110 | B1 | 5/2007 | Martin et al. |
| 7,228,179 | B2 | 6/2007 | Campen et al. |
| 7,571,007 | B2 | 8/2009 | Erickson et al. |
| 8,498,698 | B2 * | 7/2013 | Donofrio ................. A61N 1/37 607/2 |

(Continued)

FOREIGN PATENT DOCUMENTS

WO 2001093953 A1 12/2001

*Primary Examiner* — Michael W Kahelin
*Assistant Examiner* — Naveed R. Kolia
(74) *Attorney, Agent, or Firm* — The Small Patent Law Group LLC; Dean D. Small

(57) ABSTRACT

A neurostimulation (NS) system and method are provided. The system includes a power supply having positive and negative terminals. The negative terminal defines a reference ground. An array of electrodes includes first and second active electrodes for delivering stimulation therapy configured to be located proximate to neural tissue of interest that is associated with a target region. A control circuit is configured to control delivery of stimulation current for a NS therapy between the first and second electrodes. A current regulator (CR) circuit is connected to, and configured to control current flow through, at least the first electrode during delivery of the stimulation therapy under direction of the control circuit. A floating power supply is connected across power supply terminals of the CR circuit. The CR circuit and floating power supply are coupled to a floating ground node that is electrically separate from the reference ground.

18 Claims, 8 Drawing Sheets

(56) References Cited

U.S. PATENT DOCUMENTS

| | | |
|---|---|---|
| 9,054,436 B2 | 6/2015 | Swanson et al. |
| 9,533,164 B2 | 1/2017 | Erickson et al. |
| 2003/0199944 A1* | 10/2003 | Chapin ................. G06N 3/061 607/48 |
| 2006/0170486 A1 | 8/2006 | Tranchina et al. |
| 2011/0160803 A1* | 6/2011 | Stessman ................. A61N 1/37 607/62 |
| 2013/0325085 A1* | 12/2013 | Carbunaru ......... A61N 1/37211 607/62 |
| 2019/0170832 A1* | 6/2019 | Kravljaca ............... G05F 1/595 |

* cited by examiner

NEUROSTIMULATION METHOD AND SYSTEM WITH CURRENT REGULATOR BIASED BY FLOATING POWER SUPPLY

RELATED APPLICATION

The following application relates to and is expressly incorporated herein by reference in its entirety (hereafter referred to as "Co-Pending Related Application"):

U.S. patent application Ser. No. 16/401,943, titled "NEUROSTIMULATION METHOD AND SYSTEM FOR ACTIVE EMULATION OF PASSIVE DISCHARGE IN PRESENCE OF MRI/EMI INTERFERENCE".

BACKGROUND OF THE INVENTION

Embodiments herein generally relate to neurostimulation (NS) methods and systems and more particularly to regulating stimulation current during NS therapy and electrode discharge in the presence of magnetic resonance imaging (MRI) scanners and/or electromagnetic interference (EMI).

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Of course, stimulation systems may be used in stimulating areas of the human body other than the spinal cord, such as for deep brain stimulation, muscle stimulation, etcetera. Stimulation systems often comprise a pulse generator coupled to one or more percutaneous leads having a plurality of electrodes disposed in an area in which neurostimulation is desired. Alternatively, stimulation systems may comprise micro-stimulation systems in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF) system. A typical IPG configuration comprises a surgically implanted, internally-powered pulse generator and multi-electrode lead. A typical RF system configuration comprises a surgically implanted, passive receiver and a transmitter which is worn externally. In operation, the transmitter communicates, through an RF signal, to the implanted receiver to provide stimulation energy and control. Electrodes used with the foregoing pulse generators deliver a particularized electric field to a specific region of the spinal cord or surrounding tissue. Applying such an electric field across one or more nerve bundles and/or nerve roots, if properly directed and produced at the necessary levels, can "mask" certain forms of chronic pain. Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the stimulation waveform (collectively "stimulation setting"). The waveform properties generally include a stimulation frequency, a stimulation pulse width, and stimulation amplitude information. Implantation of all or a portion of a stimulation system, e.g., a stimulation system including a fully implanted IPG or a RF system receiver/transmitter, necessarily requires a neurostimulation patient to undergo an implantation surgery. Additionally, routing a lead sub-dermally between an implanted pulse generator and the tissue area to be stimulated typically requires a relatively invasive procedure, such as a tunneling procedure. Likewise, explanting all or a portion of a stimulation system requires a neurostimulation patient to again undergo the trauma of surgery.

However, conventional IPGs experience certain limitations, particularly in the presence of electromagnetic interference (EMI) including, but not limited to interference caused by magnetic resonance imaging (MRI) scanners. For example, when a patient, who has an implanted IPG, undergoes an MRI scan, the EMI from the MRI system may generate unwanted voltage potentials within the IPG and across the electrodes of the NS lead. Among other issues, if the IPG continues to attempt to deliver an NS therapy while a patient is undergoing an MRI scan, the EM fields from the MRI scanner may induce added voltage potentials across the electrodes, thereby changing the magnitude and nature of the delivered NS therapy in unpredictable, undesired and uncontrollable manners.

To avoid an unpredictable, uncontrolled or undesirable current flow before, during and after stimulation delivery of the NS therapy, many conventional NS systems have stimulation therapy turned off during an MRI scan. Additionally or alternatively, the IPG may be programmed to include a separate special NS therapy that is configured specifically for the purpose of being delivered during the presence of an MRI scan. Adding an NS therapy specifically tailored to an MRI scan introduces an undesired additional burden in programming of the IPG, as well as may require additional memory and/or circuitry to implement the MRI specific NS therapy.

A goal continues to remain to improve performance of NS systems, particularly in the presence of EMI. Among other things, it is desirable to reduce the physical circuit area and complexity of electronic control circuits, as well as to simplify NS system programming for therapy delivery. A need remains for improved methods and systems for delivering consistent, intended, and predictable NS therapy and for optimally managing discharge of voltage buildups on stimulation electrodes even while in the presence of EMI events, such as what occurs from an MRI scanner.

SUMMARY

In accordance with embodiments herein, a neurostimulation (NS) system is provided. The system includes a power supply having positive and negative terminals. The negative terminal defines a reference ground. An array of electrodes are positioned within a patient. The array of electrodes includes first and second active electrodes for delivering stimulation therapy configured to be located proximate to neural tissue of interest that is associated with a target region. A control circuit is configured to control delivery of stimulation current for a NS therapy between the first and second electrodes. A current regulator (CR) circuit is connected to, and configured to control current flow through, at least the first electrode during delivery of the stimulation therapy under direction of the control circuit. A floating power supply is connected across power supply terminals of the CR circuit. The CR circuit and floating power supply are coupled to a floating ground node that is electrically separate from the reference ground.

Optionally, during delivery of the stimulation therapy, the floating ground node may be electrically separate from the negative terminal of the power supply in order that a voltage potential at the floating ground node drifts relative to a voltage potential at the negative terminal to maintain a stimulation profile during delivery of the stimulation therapy while in a presence of an EMI event. During a discharge operation, the floating ground node may be electrically separate from the negative terminal of the power supply in order that a voltage potential at the floating ground node and a voltage potential across the voltage supply terminals of the CR circuit maintain an actively emulated passive discharge (AEPD) profile during the discharge operation.

Optionally, the floating power supply may include a charge pump and a switch network. The switch network may be configured to connect the charge pump to the power supply when charging the charge pump. The charge pump may be configured to be disconnected from the power supply when powering the CR circuit during an EMI event. A reference voltage source may be configured to supply a reference voltage as a first input to the CR circuit. The CR circuit may have a second input to receive a feedback signal. The CR circuit may be configured to regulate the stimulation current flow through the first electrode. The CR circuit may comprise an error amplifier and a transistor. The transistor may be configured to regulate the stimulation current flow through the first and second electrodes based on an output of the error amplifier to maintain the stimulation profile while in a presence of an EMI event.

Optionally, when in a presence of an EMI event, the voltage at the floating ground node may drift upward and downward to inversely track the induced interference voltages caused by the EMI and based thereon voltages may drift upward and downward by related amounts at the first and second electrodes and the feedback signal. When in a discharge configuration, a first input terminal of the CR circuit may connect to a voltage level shift component, while a second input terminal is connected to a reference voltage source. a negative terminal of the reference voltage source may be connected to the floating ground node. The voltage level shift component may be connected between the first input terminal and the second electrode. The first electrode may be connected to a positive terminal of a voltage multiplier. A negative terminal of the voltage multiplier may be connected to the floating ground node. An EMI antenna may be configured to sense and mitigate interference from EMI. The control circuit may be configured to deliver the NS therapy continuously over successive therapy delivery intervals that may be separated by corresponding successive discharge operations while in the presence of the EMI event.

In accordance with embodiments herein, a method for managing neurostimulation (NS) is provided. The method may provide an array of electrodes including first and second active electrodes for stimulation therapy delivery configured to be located proximate to neural tissue of interest that is associated with a target region. The method may provide a power supply having positive and negative terminals. The negative terminal defines a reference ground. During delivery of the stimulation therapy in a presence of an EMI event the method controls delivery of a stimulation of an NS therapy during a therapy delivery interval between the first and second electrodes. The method utilizes a current regulator (CR) circuit to control current flow through at least the first electrode during delivery of the stimulation therapy, supplies supplying power to the CR circuit from a floating power supply connected across power supply terminals of the CR circuit and couples the CR circuit and floating power supply to a floating ground node that is electrically separate from the reference ground.

Optionally, during delivery of the stimulation therapy, a voltage potential at the floating ground node may drift relative to a voltage potential at the negative terminal to maintain a stimulation profile during delivery of the stimulation while in a presence of an EMI event. During a discharge operation, may maintain the floating ground node electrically separate from the negative terminal of the power supply in order that a voltage potential at the floating ground node and a voltage potential across the power supply terminals of the CR circuit may maintain an actively emulated passive discharge (AEPD) profile during the discharge operation.

Optionally, the method may provide the floating power supply with a charge pump. The method may connect the power supply to the charge pump when charging the charge pump and may disconnect the power supply from the charge pump when powering the CR circuit during an EMI event. The method may supply a reference voltage as a first input to the CR circuit and may supply a feedback signal as a second input to the CR circuit, regulating the stimulation current flow through the first electrode. The CR circuit may comprise an error amplifier and a transistor. The transistor may be configured to regulate the current flow through the first and second electrodes based on an output of the error amplifier to maintain the stimulation profile while in a presence of an EMI event. When in a presence of an EMI event, the voltage at the floating ground node may drift upward and downward to inversely track the induced interference voltages caused by the EMI and based thereon voltages may drift upward and downward by related amounts at the first and second electrodes and the feedback signal.

Optionally, when in a discharge configuration, a first input terminal of the CR circuit may connect to a voltage level shift component, while a second input terminal of the CR circuit may be connected to a reference voltage source. A negative terminal of the reference voltage source may be connected to the floating ground node. The voltage level shift component may be connected between the first input terminal and the second electrode. The first electrode may be connected to a positive terminal of a voltage multiplier. A negative terminal of the voltage multiplier may be connected to the floating ground node. The method may provide an EMI antenna, utilized for sensing and mitigating the interference from EMI. The method may deliver the NS therapy continuously over successive therapy delivery intervals that may be separated by corresponding successive discharge operations while in the presence of the EMI event.

DETAILED DESCRIPTION

Figure 1:
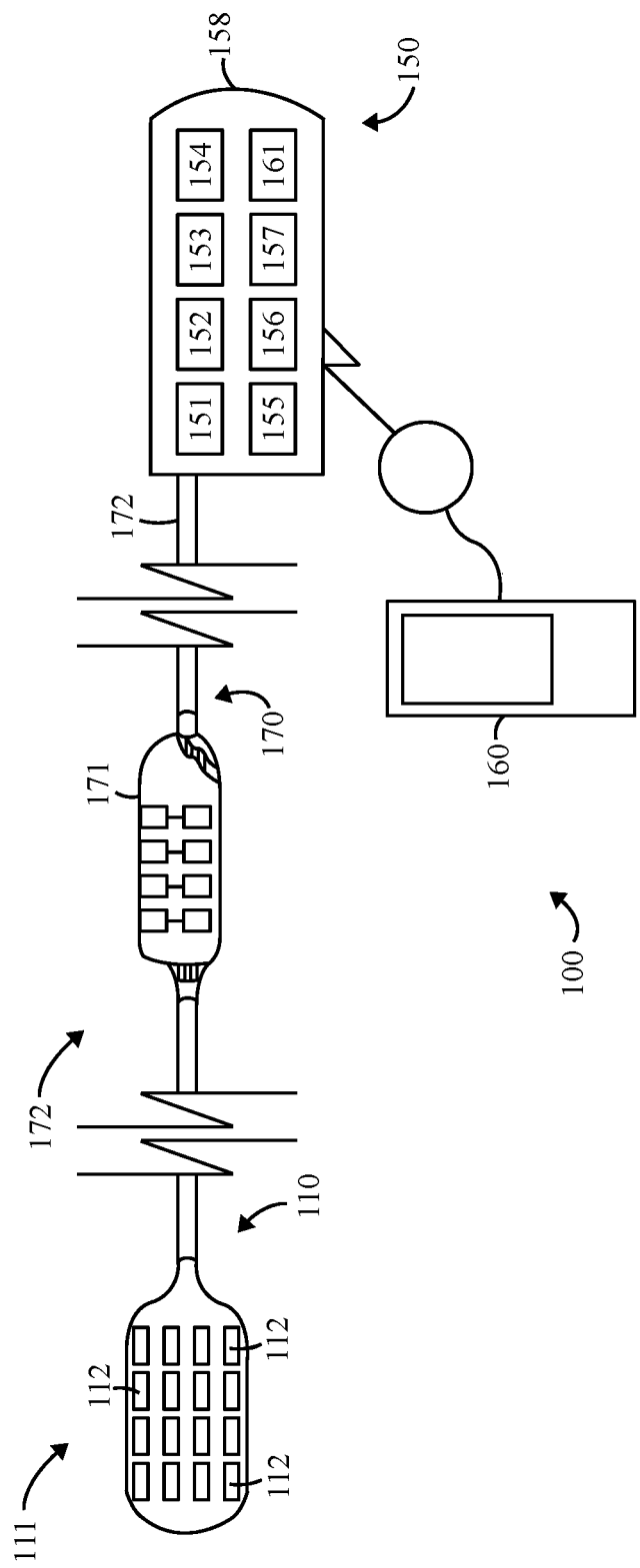
FIG. 1 illustrates a schematic block diagram of an embodiment of a neurostimulation system in accordance with embodiments herein.
Figure 2A:
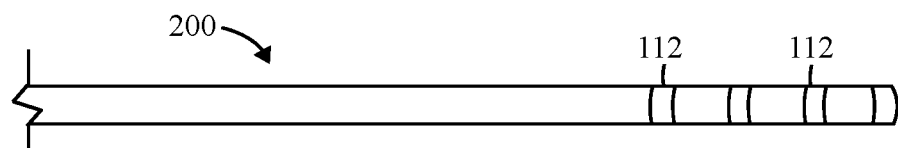
FIGS. 2A-2I, respectively, depict stimulation portions for inclusion at the distal end of the lead in accordance with embodiments herein.
Figure 2B:
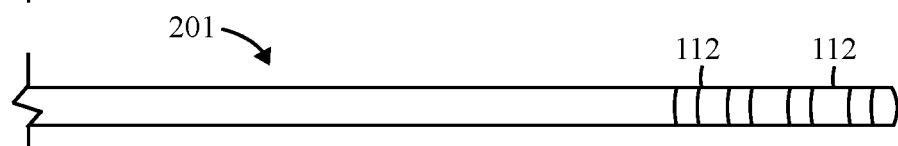
Figure 2C:
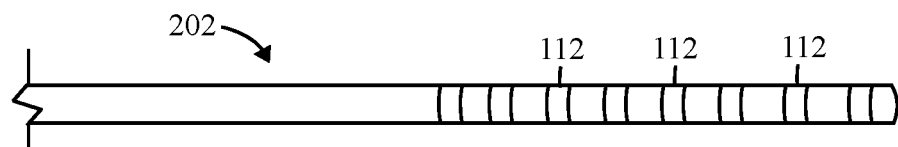
Figure 2D:
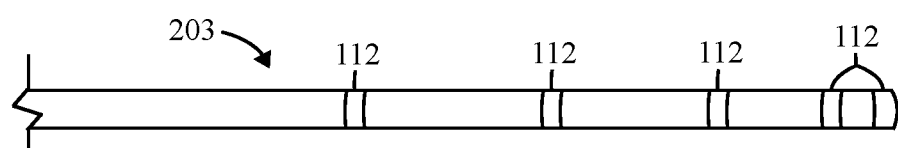
Figure 2E:
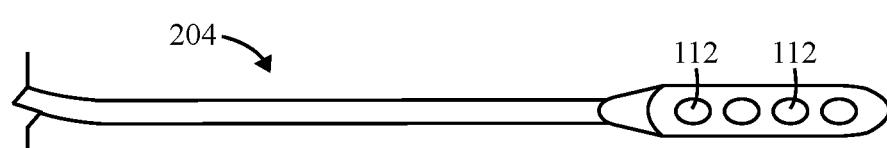
Figure 2F:
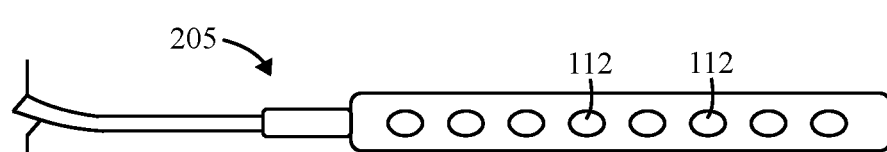
Figure 2G:
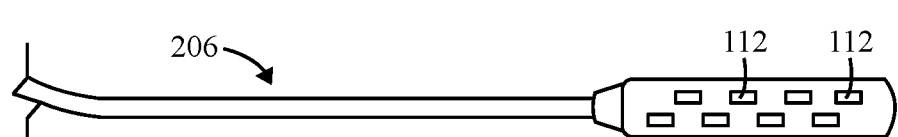
Figure 2H:
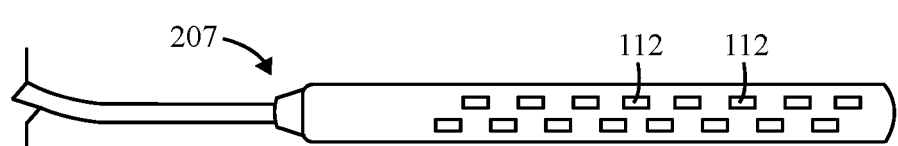
Figure 2I:
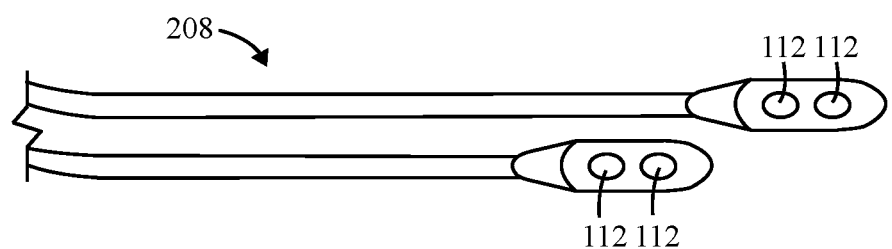

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Terms

The term "floating", as used in connection with describing a ground, ground node, power supply, and connection, shall mean that a voltage at the corresponding ground, ground node, power supply, and connection is permitted to drift, or otherwise fluctuate, upward and downward and is not tied to a fixed voltage reference (e.g., 0 V). For example, a floating ground node shall mean the ground node is not tied to a fixed ground voltage and is not tied to a negative terminal of a battery. As a further example, when a negative terminal of the battery defines a fixed reference ground, a floating ground or floating ground node is not electrically connected to a same ground as the negative terminal of the battery. As a further example, the term "floating power supply" shall mean a power supply for which the negative terminal is not electrically connected to a same ground as the negative terminal of the battery, but instead is allowed to drift upward and downward.

The term "stimulation parameters" refer to electrical characteristics of the NS therapy. The stimulation parameters may represent a pulse width, a frequency, an amplitude, a duty cycle, an NS therapy type, and/or the like. The NS therapy type can represent a characteristic of the NS therapy delivered by the NS system. The characteristic may correspond to stimulation and/or pulse patterns of the NS therapy. The pulse patterns may be a burst stimulation waveform or a tonic stimulation waveform of the NS therapy. The tonic stimulation waveform represents a single pulse repeated at a rate defined by the duty cycle. The burst stimulation waveform represents a series of pulses grouped to form a pulse train. The pulse train may be repeated at a cycle rate defined by the duty cycle.

The term "active," when referring to an electrode, shall mean a stimulation electrode that is utilized to deliver stimulation in connection with one or more types of therapy for the present patient.

The term "inactive," when referring to an electrode, shall mean an unused, non-stimulation electrode that is not used to delivery stimulation in connection with any type of therapy for the present patient. The inactive electrode may also be referred to as an unused or non-stimulation electrode as no therapy is intended to be delivered through the electrode. As explained herein, one or more inactive electrodes are used as part of a feedback control loop in connection with mitigating the effects of MRI/EMI interference.

The terms "electromagnetic interference" and "EMI" shall mean interference experienced by an NS system when exposed to electromagnetic fields. One non-limiting example is when an NS system is in the presence of an operating magnetic resonance imaging (MRI) scanner, the NS system will experience EMI.

The terms "actively emulated passive discharge profile" and "AEPD profile" refer to a shape of a curve plotting charge, voltage and/or current over time while discharging the residual voltages which have built up during stimulation on the active anode and cathode electrodes of an NS system. The AEPD profile is intended to mimic the shorting together of the active electrodes for discharge in conventional NS systems, but which allows a high impedance loop to exist during electrode discharge while the NS system is exposed to EMI. Because of this high impedance loop behavior, the AEPD profile behavior provides substantially improved MRI/EMI immunity and patient safety as compared to conventional NS systems while electrode discharge is performed after stimulation therapy delivery, particularly in Monopolar stimulation configurations for DBS therapy which utilize the NS system Case/Can as the anode electrode.

Overview

In accordance with embodiments herein, methods and systems implement a current regulator (CR) circuit, within an NS system, that maintains a high impedance loop between the Case/Can and the stimulation electrodes when in the presence of electromagnetic interference. By maintaining the high impedance loop, the NS system avoids degradation of the stimulation therapy, avoids unintended stimulation, and avoids patient safety concerns. As an example, EMI may introduce interference voltages between the IPG can/case and the electrodes on the lead at levels as high as +/−10-11 V during an MRI scan for an implantable SCS device. Conventional approaches handle this interference difficulty by directing the SCS patient to disable their neural stimulation therapy before the MRI scan and to have the IPG devised to be placed into an MRI safe mode of operation.

Embodiments herein overcome disadvantages of conventional NS systems and, while in the presence of EMI, allow and maintain effective and safe control during delivery of the stimulation therapy and during discharge operations. In connection therewith, a current regulator of the NS system is powered by a floating power supply that is implemented by one or more charge pumps. An EMI antenna can be utilized to sense and mitigate interference voltages induced by EMI. By way of example, the EMI antenna may include one or more Kelvin connect electrodes or unused electrodes in a NS Lead that are not being used to deliver stimulation therapy to the patient. The unused electrode can operate as the EMI antenna to sense and mitigate interference voltages induced by EMI. Additionally or alternatively, the EMI antenna may be constructed as a "dummy" wire provided within the lead or routed with insulation substantially alongside the outside of the NS lead and arranged to extend alongside other stimulation wires in the NS lead. The dummy wire may not electrically conduct to human tissue, and thus may not be considered to be an "electrode." Based on the voltage sensed at the EMI antenna, a control circuit can adjust up/down a common mode voltage applied to the patient tissue at the IPG Can/Case, such that interference voltages induced by EMI do not degrade stimulation therapy. In accordance herewith, neural stimulation therapy may be applied continuously and with a desired control for DBS and SCS patients during MRI scans and/or while in the presence of other types of EMI. Embodiments herein respond automatically to a presence of EMI, without patient interaction, that would otherwise be necessary in prior systems to mitigate interference. Hence, embodiments herein provide a more robust and reliable mechanism for maintaining neural stimulation therapy in the presence of EMI. Embodiments herein exhibit very efficient performance, while utilizing a limited circuit area utilized within the NS system and provide a relatively non-complex electronic control circuit. The CR circuit provides an improved and optimized control architecture for active emulation of passive discharge in the presence of EMI, which provides substantial advantages in minimizing undesirable therapeutic side effects during electrode discharge, especially for DBS therapy applications. For further details on these advantages, see U.S. patent application Ser. No. 16/401,943, titled "NEUROSTIMULATION METHOD AND SYSTEM FOR ACTIVE EMULATION OF PASSIVE DISCHARGE IN PRESENCE OF MRI/EMI INTERFERENCE".

By utilizing a floating ground node and floating power supply, embodiments herein allow the operating voltages for the components herein to drift upward and downward, such as when exposed to EMI interference, thereby affording sufficient operating range (also referred to as "headroom") for components such as the charge pump, error amplifier, DAC reference, voltage multiplier and other components. By allowing the floating ground node to drift upward and downward, such as when exposed to EMI interference, embodiments herein avoid the charge pump, error amplifier, DAC reference, voltage multiplier and other components from reaching or exceeding the voltage range limits of such components.

FIG. 1 depicts a schematic block diagram of an embodiment of a neurostimulation (NS) system 100. The NS system 100 is configured to generate electrical stimulation (e.g., excitation pulses) for application to neural tissue of the patient according to one embodiment. For example, the NS system 100 may be adapted to stimulate spinal cord tissue, dorsal root, dorsal root ganglion (DRG), peripheral nerve tissue, deep brain tissue, cortical tissue, cardiac tissue, digestive tissue, pelvic floor tissue, and/or any other suitable neural tissue of interest within a body of a patient.

The NS system 100 includes an implantable pulse generator (IPG) 150 that is adapted to generate electrical stimulation for application to tissue of a patient. The IPG 150 typically comprises a metallic housing or Can 158 that encloses a controller circuit 151, pulse generating circuitry 152, a charging coil 153, a battery 154, a communication circuit 155, battery charging circuitry 156, switching circuitry 157, memory 161, and/or the like. The communication circuit 155 may represent hardware that is used to transmit and/or receive data along a uni-directional communication link and/or bi-directional communication link (e.g., with an external device 160).

The controller circuit 151 is configured to control the operation of the IPG 150. The controller circuit 151 may include one or more processors, a central processing unit (CPU), one or more microprocessors, or any other electronic component capable of processing input data according to program instructions. Optionally, the controller circuit 151 may include and/or represent one or more hardware circuits or circuitry that include, are connected with, or that both include and are connected with one or more processors, controllers, and/or other hardware logic-based devices. Additionally or alternatively, the controller circuit 151 may execute instructions stored on a tangible and non-transitory computer readable medium (e.g., the memory 161).

The IPG 150 may include a separate or an attached extension component 170. The extension component 170 may be a separate component. For example, the extension component 170 may connect with a "header" portion of the IPG 150, as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within the connector portion 171 or within the IPG header for electrical connection with respective connectors. The pulses originating from the IPG 150 are provided to the one or more leads 110. The pulses are then conducted through the conductors of the lead 110 and applied to tissue of a patient via an electrode array 111. Any suitable known or later developed design may be employed for connector portion 171.

The electrode array 111 may be positioned on a paddle structure of the lead 110. For example, in a planar formation on a paddle structure as disclosed in U.S. Provisional Application No. 51/791,288, entitled, "PADDLE LEADS FOR NEUROSTIMULATION AND METHOD OF DELIVERING THE SAME," which is expressly incorporated herein by reference. The electrode array 111 includes a plurality of electrodes 112 aligned along corresponding rows and columns. Each of the electrodes 112 are separated by non-conducting portions of the paddle structure, which electrically isolate each electrode 112 from an adjacent electrode 112. The non-conducting portions may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The electrodes 112 may be configured to emit pulses in an outward direction.

Optionally, the IPG 150 may have one or more leads 110 connected via the connector portion 171 of the extension component 170 or within the IPG header. For example, a DRG stimulator, a steerable percutaneous lead, and/or the like. Additionally or alternatively, the electrodes 112 of each lead 110 may be configured separately to emit excitation pulses.

Leads

FIGS. 2A-2I, respectively, depict stimulation portions 200-208 for inclusion at the distal end of the lead 110. For example, the stimulation portions 200-208 depict a conventional stimulation portion of a "percutaneous" lead with multiple electrodes 112. The stimulation portions 200-208 depict a stimulation portion including several segmented electrodes 112. Example fabrication processes are disclosed in U.S. patent application Ser. No. 14/895,096, entitled, "METHOD OF FABRICATING STIMULATION LEAD FOR APPLYING ELECTRICAL STIMULATION TO TISSUE OF A PATIENT," which is incorporated herein by reference. Stimulation portions 204-208 include multiple electrodes 112 on alternative paddle structures than shown in FIG. 1.

In connection to FIG. 1, the lead 110 may include a lead body 172 of insulative material about a plurality of conductors within the material that extend from a proximal end of lead 110, proximate to the IPG 150, to its distal end. The conductors electrically couple a plurality of the electrodes 112 to a plurality of terminals (not shown) of the lead 110. The terminals are adapted to receive electrical pulses and the electrodes 112 are adapted to apply the pulses to the stimulation target of the patient. It should be noted that although the lead 110 is depicted with sixteen electrodes 112, the lead 110 may include any suitable number of electrodes 112 (e.g., less than sixteen, more than sixteen) as well as terminals, and internal conductors.

Although not required for all embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 40% at forces of about 0.5, 1.0, and/or 2.0 pounds of stretching force. Fabrication techniques and material characteristics for "body compliant" leads are disclosed in greater detail in U.S. Provisional Patent Application No. 50/788,518, entitled "Lead Body Manufacturing," which is expressly incorporated herein by reference.

For implementation of the components within the IPG 150, a processor and associated charge control circuitry for an IPG is described in U.S. Pat. No. 6,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 6,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different pulses on different electrodes 112 may be generated using a single set of the pulse generating circuitry 152 using consecutively generated pulses according to a "multi-stimset program" as is known in the art. Complex stimulation parameters may be employed such as those described in U.S. Pat. No. 6,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., the tonic stimulation waveform, the burst stimulation waveform) that include generated and delivered stimulation pulses through various electrodes 112 of the one or more leads 110 as is also known in the art. Various sets of stimulation parameters may define the characteristics and timing for the pulses applied to the various electrodes 112 as is known in the art. Although constant current excitation pulse generating circuitry is contemplated for some embodiments, any other suitable type of pulse generating circuitry may be employed such as constant voltage pulse generating circuitry.

The external device 160 may be implemented to charge/recharge the battery 154 of the IPG 150 (although a separate recharging device could alternatively be employed), to access the memory 161, to program the IPG 150 when implanted within the patient, to communicate triggering events to the NS system 100, and/or the like. The external device 160 may be a workstation, a portable computer, an NS system programmer, a PDA, a cell phone, a smart phone, a tablet, and/or the like.

Figure 3:
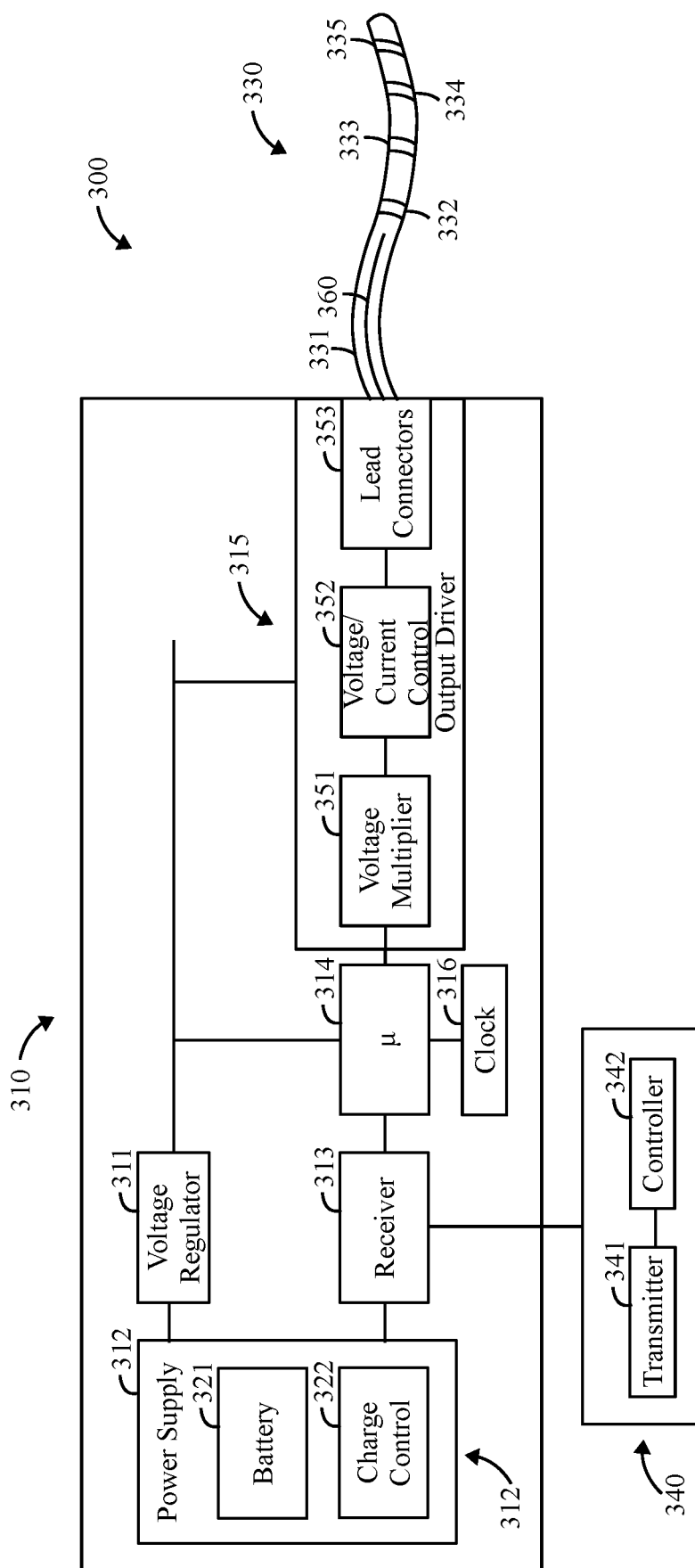
FIG. 3 illustrates a stimulation system adapted according to an embodiment and is shown in a high-level functional block diagram in accordance with embodiments herein.

FIG. 3 illustrates a stimulation system 300 adapted according to an embodiment and is shown in a high-level functional block diagram. In operation, stimulation system 300 generates and applies a stimulus to tissue or a certain location of a body. Stimulation system 300 of the illustrated embodiment includes a generator portion, shown as implantable pulse generator (IPG) 310, providing a stimulation or energy source, stimulation portion, shown as lead 330, for application of the stimulus pulse(s), and an optional external controller, shown as programmer/controller 340, to program and/or control implantable pulse generator 310 via a wireless communications link. IPG 310 may be implanted within a living body (not shown) for providing electrical stimulation from IPG 310 to a selected area of the body via lead 330, perhaps under control of external programmer/controller 340. It should be appreciated that, although lead 330 is illustrated to provide a stimulation portion of stimulation system 300 configured provide stimulation remotely with respect to the generator portion of stimulation system 300, a lead as described herein is intended to encompass a variety of stimulation portion configurations. For example, lead 330 may comprise a microstimulator electrode disposed adjacent to a generator portion. Furthermore, a lead configuration may include more (e.g., 7, 16, 32, etcetera) or fewer (e.g., 1, 2, etcetera) electrodes than those represented in the illustrations. As explained in the Co-Pending Related Application, the lead 330 may include an EMI antenna configured to provide an EMI feedback signal indicative of an amount of interference voltage induced by the EMI. The EMI antenna may be implemented in various manners, such as utilizing an inactive electrode (e.g., one of electrodes 332-335) and/or utilizing a non-electrode segment of wire 360 provided within the lead or routed with insulation substantially alongside the outside of the lead 330. The wire 360 is not connected to any of the electrodes 332-335 and may be held within a body of the lead 330 to prevent the wire 360 from contacting human tissue. Alternatively, the wire 360 may be fully insulated and routed substantially alongside the outside of the lead 330.

IPG 310 may comprise a self-contained implantable pulse generator having an implanted power source such as a long-lasting or rechargeable battery. Alternatively, IPG 310 may comprise an externally-powered implantable pulse generator receiving at least some of the required operating power from an external power transmitter, preferably in the form of a wireless signal, which may be radio frequency (RF), inductive, etc.

IPG 310 of the illustrated embodiment includes voltage regulator 311, power supply 312, receiver 313, microcontroller (or microprocessor) 314, output driver circuitry 315, and clock 316, as are described in further detail below. Power supply 312 provides a source of power, such as from battery 321 (battery 321 may comprise a non-rechargeable (e.g., single use) battery, a rechargeable battery, a capacitor, and/or like power sources), to other components of IPG 310, as may be regulated by voltage regulator 311. Charge control 322 of embodiments provides management with respect to battery 321. Receiver 313 of embodiments provides data communication between microcontroller 314 and controller 342 of external programmer/controller 340, via transmitter 341. It should be appreciated that although receiver 313 is shown as a receiver, a transmitter and/or transceiver may be provided in addition to or in the alternative to receiver 313, depending upon the communication links desired. Receiver 313 of embodiments, in addition to or in the alternative to providing data communication, provides a conduit for delivering energy to power supply 312, such as where RF or inductive recharging of battery 321 is implemented. Microcontroller 314 provides control with respect to the operation of IPG 310, such as in accordance with a program provided thereto by external programmer/controller 340. Output driver circuitry 315 generates and delivers pulses to selected ones of electrodes 332-335 under control of microcontroller 314. For example, voltage multiplier 351 and voltage/current control 352 may be controlled to deliver a constant current pulse of a desired magnitude, duration, and frequency to a load present with respect to particular ones of electrodes 332-335. Clock 316 preferably provides system timing information, such as may be used by microcontroller 314 in controlling system operation, as may be used by voltage multiplier 351 in generating a desired voltage, etcetera.

Lead 330 of the illustrated embodiment includes lead body 331, preferably incarcerating a plurality of internal conductors coupled to lead connectors (not shown) to interface with lead connectors 353 of IPG 310. Lead 330 further includes electrodes 332-335, which are preferably coupled to the aforementioned internal conductors. The internal conductors provide electrical connection from individual lead connectors to each of a corresponding one of electrodes 332-335. In the exemplary embodiment the lead 330 is generally configured to transmit one or more electrical signals from IPG 310 for application at, or proximate to, a spinal nerve or peripheral nerve, brain matter, muscle, or other tissue via electrodes 332-335. IPG 310 is capable of controlling the electrical signals by varying signal parameters such as intensity, duration and/or frequency in order to deliver a desired therapy or otherwise provide operation as described herein.

Although the embodiment illustrated in FIG. 3 includes 4 electrodes, it should be appreciated that any number of electrodes, and corresponding conductors, may be utilized according to some embodiments. Moreover, various types, configurations and shapes of electrodes (and lead connectors) may be used according to some embodiments. An optional lumen (not shown) may extend through the lead 330, such as for use in delivery of chemicals or drugs or to accept a stylet during placement of the lead within the body. Additionally or alternatively, the lead (stimulation portion) and IPG (generator portion) may comprise a unitary construction, such as that of a microstimulator configuration.

As mentioned above, external programmer/controller 340 of embodiments provides data communication with IPG 310, such as to provide control (e.g., adjust stimulation settings), provide programming (e.g., alter the electrodes to which stimulation pulses are delivered), etcetera. Accordingly, external programmer/controller 340 of the illustrated embodiment includes transmitter 341, for establishing a wireless link with IPG 310, and controller 342, to provide control with respect to programmer/controller 340 and IPG 310. Additionally or alternatively, external programmer/controller 340 may provide power to IPG 310, such as via RF transmission by transmitter 341. Optionally, however, a separate power controller may be provided for charging the power source within IPG 310.

Additional detail with respect to pulse generation systems and the delivery of stimulation pulses may be found in U.S. Pat. No. 5,609,031, entitled "MULTIPROGRAMMABLE TISSUE STIMULATOR AND METHOD," the disclosure of which is hereby incorporated herein by reference. Similarly; additional detail with respect to pulse generation systems and the delivery of stimulation pulses may be found in the above referenced patent application entitled "MULTI-PROGRAMMABLE TRIAL STIMULATOR."

Having generally described stimulation system 300 above, the discussion which follows provides detail with respect to various functional aspects of stimulation system 300 according to some embodiments. Although the below embodiments are described with reference to stimulation system 300, and IPG 310 thereof, it should be appreciated that the concepts described herein are not limited to application to the exemplary system and may be used in a wide variety of medical devices.

Voltage Multiplier Output Voltage

FIG. 3 illustrates a block diagram of the voltage/current control of the NS system in more detail in accordance with an embodiment herein. The voltage/current control 352 provides automatic and/or manual voltage control, allowing incrementing and decrementing of the output voltage, with respect to voltage multiplier 351. In a manual mode of one embodiment, the output voltage setting is controlled by microcontroller 314 providing a set control signal to voltage/current control 352. Accordingly, in this manual mode, microcontroller 314 is involved in the changes to the output voltage of voltage multiplier 351 in terms of incrementing or decrementing the values. However, in an automatic mode of one embodiment, voltage/current control 352 controls the changes to the output voltage of voltage multiplier 351, and thus there need not be any processing overhead on the part of microcontroller 314 to determine the optimal value for the output voltage of voltage multiplier 351.

Figure 4:
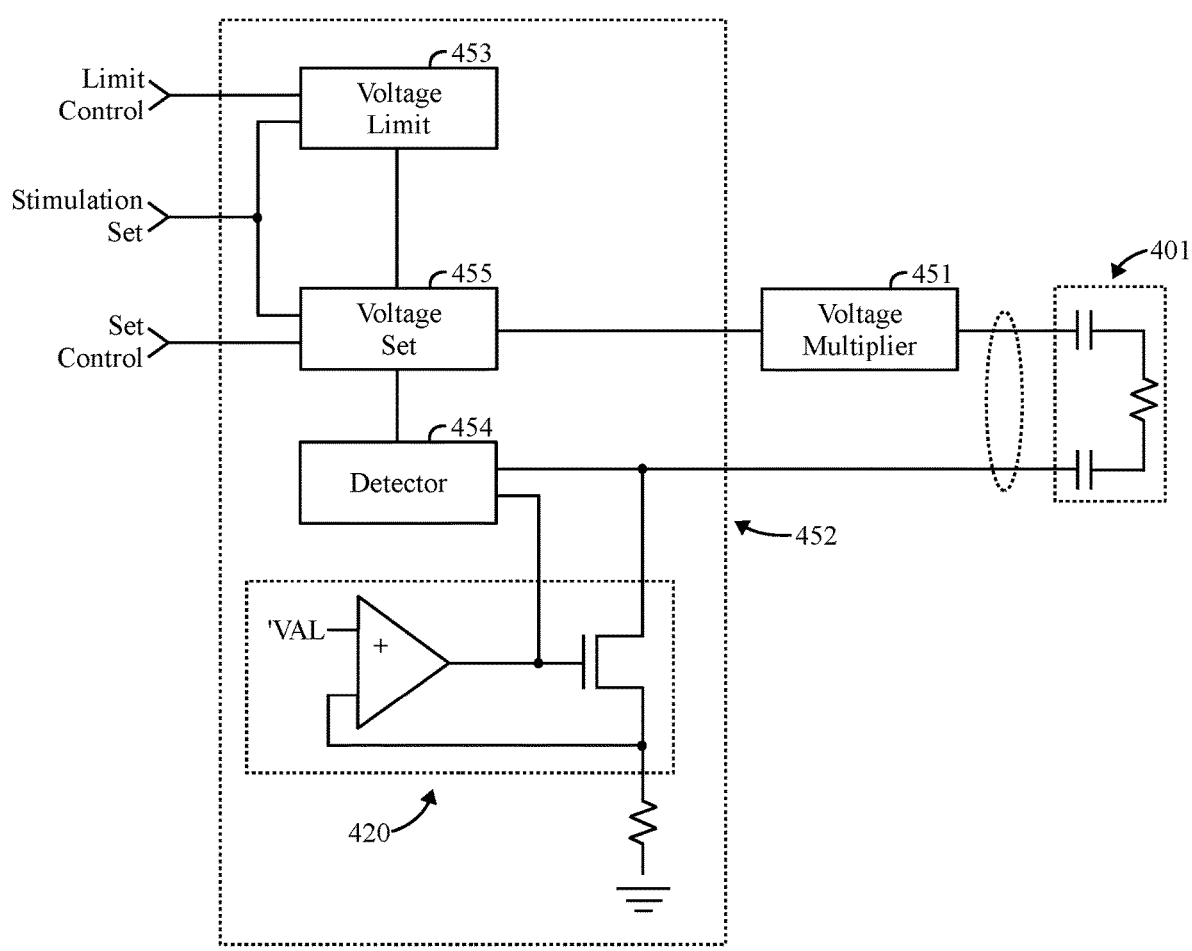
FIG. 4 illustrates detail of a stimulation system with respect to an embodiment of voltage/current control for providing voltage multiplier voltage control in accordance with embodiments herein.

Voltage multiplier 351 utilized according to some embodiments preferably comprises a fractional voltage multiplier, such as may provide output voltages in fractional multiples of a supply voltage. Additional detail with respect to fractional voltage multipliers as may be utilized according to some embodiments is provided in U.S. Pat. No. 6,180,760 entitled "FRACTIONAL VOLTAGE CONVERTER", filed Apr. 12, 2005, the complete subject matter of which is expressly incorporated herein by reference. In operation of IPG 310 according to some embodiments, a goal is to provide a power source to deliver a particular amount of current to load 401 (such as may comprise a portion of a human body into which lead 330 is implanted) via selected ones of electrodes 332-335. It should be appreciated that, as set forth in Ohm's law, a particular amount of voltage provided by voltage multiplier 351 will be needed to deliver a desired level of current through load 401 as shown in FIG. 4, which represents the electrode/tissue interface in the human body. However, providing a voltage level substantially in excess of the voltage needed to deliver the desired current may be undesirable. For example, voltage in excess to that needed for delivery of the desired current may result in inefficient use of energy from battery 321. Moreover, if the output voltage provided by voltage multiplier 351 were not set to a limit somewhat near that needed to deliver the desired current, a change in load 401 (such as by movement of lead 330 within the patient) could result in over stimulation or other undesired results.

As explained herein, the lead 330 includes an EMI antenna that is utilized to sense and mitigate interference voltages induced by EMI. By way of example, the EMI antenna may include one or more Kelvin connect electrodes or unused electrodes (e.g., any one or more of the electrodes 332-335) that are not being used to deliver stimulation therapy to the patient. Additionally or alternatively, the EMI antenna may be constructed as a "dummy" wire provided within the lead or routed with insulation substantially alongside the outside of the lead 330 and arranged to extend alongside other stimulation wires in the lead 330. The dummy wire may not electrically conduct to human tissue, and thus may not be considered to be an "electrode."

Accordingly, as shown in FIG. 4, voltage multiplier 451 and voltage/current control 452 of some embodiments cooperate to provide a voltage limited, constant current source. In providing the foregoing, voltage/current control 452 of the illustrated embodiment comprises detector 454 that monitors voltages as provided by voltage multiplier 451. When it is determined that the output voltage of voltage multiplier 451 is in excess (perhaps by a predetermined amount, such as a fractional voltage step amount) of what is needed to provide a desired current, detector 454 can provide a control signal to voltage set 455 to decrement the voltage. Voltage set 455 may, in turn, provide a control signal to voltage multiplier 451 to select an appropriate, lower, voltage (perhaps in one or more decremental steps). Similarly, when it is determined that the output voltage of voltage multiplier 451 is below what is needed to provide a desired current, detector 454 can provide a control signal to voltage set 455 to increment the voltage. Voltage set 455 may, in turn, provide a control signal to voltage multiplier 451 to select an appropriate, higher, voltage (perhaps in one or more incremental steps). Feedback circuit 420 provides detail with respect to providing information to detector 454 useful in making voltage increment/decrement determinations. As explained herein, the feedback circuit 420 includes, among other things, a current regulator that receives power from a floating power supply. The voltage limit 453 sets a limit beyond which voltage/current control 452 cannot, by itself increment the output voltage. Accordingly, when a voltage limit set by voltage limit 453 is reached, voltage/current control 452 may provide a control signal to microcontroller 314, such as to notify an operator of the limit being reached, for a determination with respect to whether the limit should be adjusted, etcetera.

Additionally, microcontroller 314, a clinician, or other user may manually provide voltage selection with respect to voltage multiplier 451, such as during trial stimulation, etcetera. Accordingly, a voltage set control signal may be provided to voltage set 455, such as by microcontroller 314, to override voltage selection as provided by detector 454, if desired.

Optionally, the voltage control circuit and/or other circuitry of the NS system may be implemented in accordance with the methods and systems described in U.S. Pat. No. 9,533,164, issuing Jan. 3, 2017, titled "METHOD FOR PROVIDING MULTIPLE VOLTAGE LEVELS DURING PULSE GENERATION AND IMPLANTABLE PULSE GENERATING EMPLOYING THE SAME", the complete subject matter of which is hereby expressly incorporated by reference in its entirety.

Current Regulation Circuit

Figure 5:
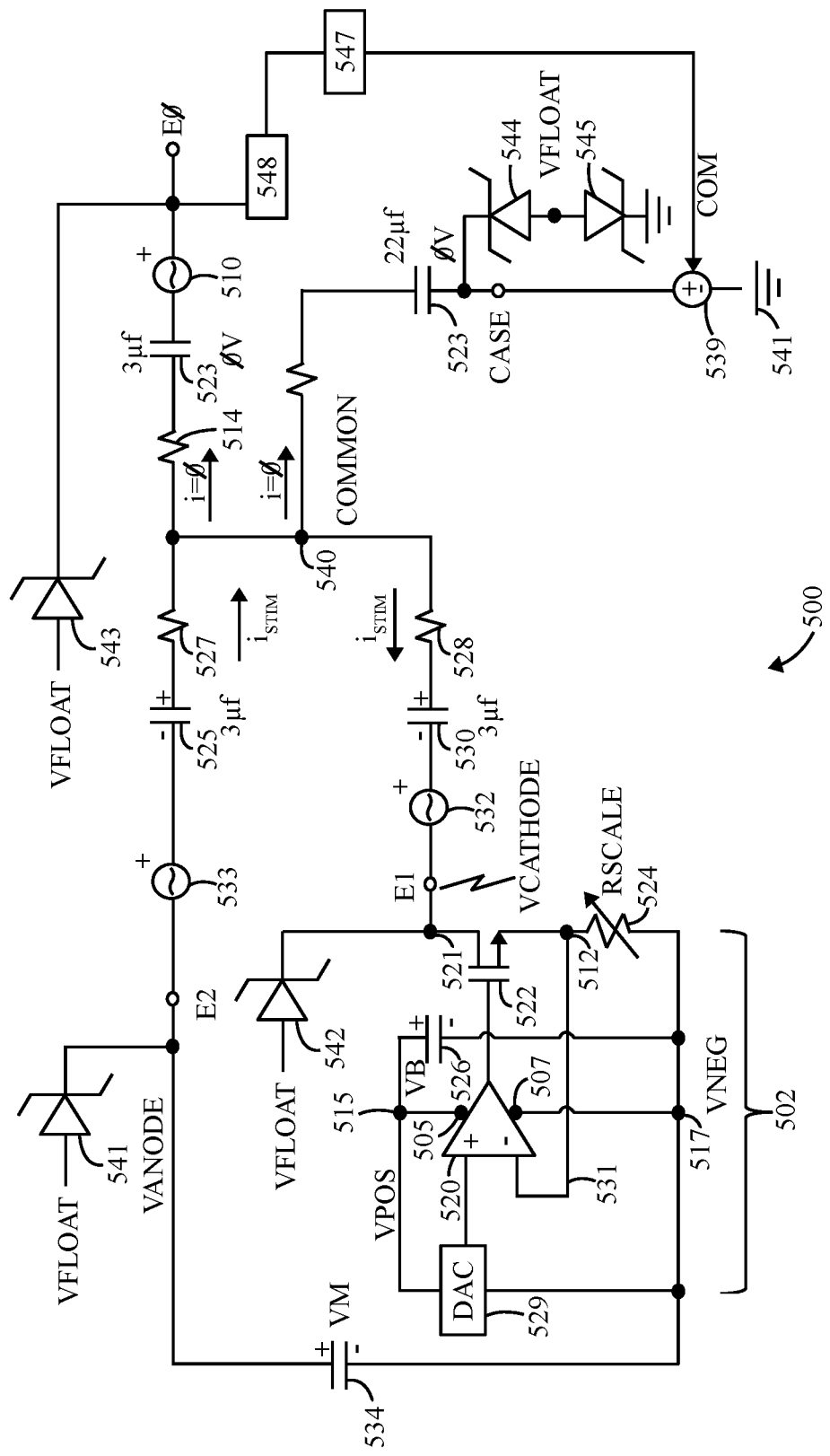
FIG. 5 illustrates a circuit diagram of the feedback circuit in a NS system along with a portion of the electrodes and circuitry when operating in a stimulation therapy delivery mode/configuration in accordance with embodiments herein.

FIG. 5 illustrates a circuit diagram of the feedback circuit of FIG. 4, along with a portion of the electrodes and circuitry when operated in a stimulation therapy delivery mode/configuration, in accordance with embodiments herein. The circuit 500 comprises an array of electrodes (designated E0, E1, E2 and Case) configured to be implanted within a patient and positioned proximate to neural tissue of interest that is associated with the target region. As a nonlimiting example, the circuit 500 may be configured to deliver a bipolar stimulation therapy for use with deep brain stimulation. For bipolar stimulation, the array of electrodes includes two or more active electrodes E1, E2. The bipolar stimulation therapy is delivered between the active electrodes E1 and E2. In the present example, the Case electrode is not utilized during bipolar stimulation therapy. Optionally, when monopolar stimulation is delivered, the Case electrode may be utilized as an anode electrode and one or more of the electrodes E1, E2 may be utilized as a cathode electrode.

The active electrode E1 is configured to be a cathode, while the active electrode E2 is configured to be an anode electrode. While the examples herein are described in connection with a single electrode E1 as the active cathode electrode, and a single electrode E2 as the anode electrode, it is recognized that in many embodiments, two or more electrodes may be utilized as anode and/or cathode electrodes. When two or more active electrodes E1 are utilized, embodiments herein may implement discharge operations in the presence of EMI events in a common discharge operation, and/or as separate discharge operations. For example, all active electrodes E1 may be connected to one another during the discharge operation in a common manner to collectively and jointly discharge any residual voltage. As another example, separate subsets of the group of active electrodes E1 may be connected to separate current regulator circuits to have residual voltages discharged separately.

The array of electrodes may include one or more inactive electrodes E0. One or more of the inactive electrodes E0 may be utilized as the EMI antenna to sense and mitigate interference voltages induced by EMI. By way of example, the EMI antenna may include one or more Kelvin connect electrodes in the NS lead that are not being used to deliver stimulation therapy to the patient. Additionally or alternatively, the EMI antenna may include a "dummy" wire provided within the lead or routed with insulation substantially alongside the outside of the NS lead and arranged to extend alongside other stimulation wires in the NS lead. The dummy wire may not electrically conduct to human tissue, and thus may not be considered an "electrode."

The circuit 500 is managed by a control circuit not shown in FIG. 5 but may be implemented at least in part by the microcontroller 314. The circuit 500 is controlled to deliver a NS therapy during stimulation delivery intervals that are separated by discharge intervals. The NS therapy is delivered through the active electrodes E1, E2 proximate to neural tissue of interest that is associated with a target region. The array of electrodes E1, E2 develop a residual voltage (e.g., an accumulated charge) over the therapy delivery intervals. The circuit 500 includes a current regulator (CR) circuit 502 that is connected to, and configured to control current flow through, at least the first electrode E1 during delivery of the stimulation therapy under direction of the control circuit. The control circuit (e.g., microcontroller 314) is coupled to the CR circuit 502 and, during the discharge operation, the control circuit is configured to manage the CR circuit 502 during an EMI event to control the discharge current flow over the discharge operation to discharge the residual voltage in a manner that follows the AEPD profile between the therapy delivery intervals. While embodiments herein are described in connection with the use of a single AEPD profile, it is recognized that more than one AEPD profile may be utilized. By way of example, the AEPD profile may be managed in accordance with the methods and systems described in a co-pending application, entitled "EMULATING PASSIVE DISCHARGE OF ELECTRODES USING A PROGRAMMABLE EXPONENTIALLY DECREASING AMPLITUDE DISCHARGE CURRENT", filed on Mar. 26, 2019, the complete subject matter of which is expressly incorporated herein by reference in its entirety.

The CR circuit 502 includes an error amplifier 520 that includes power supply terminals 505, 507 that are connected to, and receive power from, a charge pump 526 coupled between a power supply node 515 (also designated as VPOS) and a floating ground node 517 (also designated as VNEG). The charge pump 526 is connected between the floating ground node 517 and the power supply node 515. The charge pump 526 (e.g., a capacitor or capacitor bank) is selectively charged by a battery of the IPG and is configured to supply a predetermined voltage VB across the power supply terminals of the CR circuit 502. By way of example, the charge pump 526 may simply mimic the battery voltage. As explained in connection with FIG. 5, the charge pump 526 is intermittently connected to the battery of the IPG during charging operations and disconnected from the battery to allow the charge pump 526 to operate as a floating power supply for the CR circuit 502. The negative terminal of the charge pump 526 and CR circuit 502 are connected to the floating ground node 517, thereby enabling the power supply for the CR circuit 502 to move up and down in voltage (as desired in accordance with the common mode voltage $V_{com}$ defined at voltage source 539), without changing a voltage potential across the power supply terminals 515, 517 of the CR circuit 502. By utilizing a floating ground, the charge pump 526 creates a floating power supply for the CR circuit 502.

Figure 6:
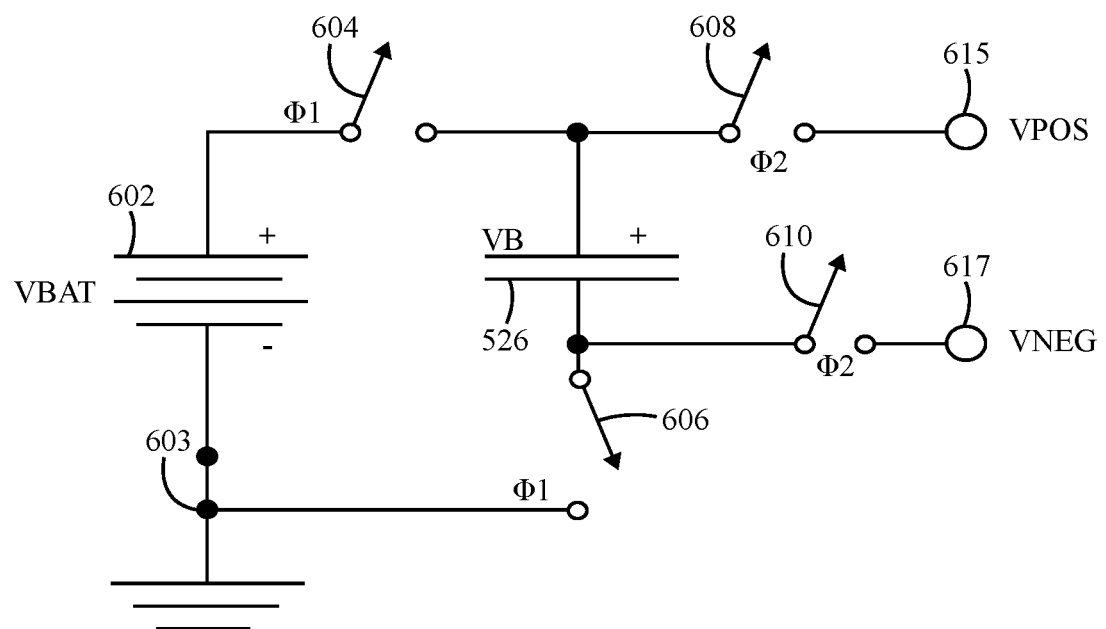
FIG. 6 illustrates a circuit diagram of an interconnection between a battery and the floating power supply in accordance with embodiments herein.

FIG. 6 illustrates a circuit diagram of an interconnection between a battery and the floating power supply 526 of FIG. 5 in accordance with embodiments herein. The floating power supply 526 includes a charge pump (illustrated as a capacitor) and a switch network that is configured to be connected to the battery when charging the charge pump. The charge pump is configured to be disconnected from the battery when powering the CR circuit during an EMI event. As one example, the positive terminal of the battery 602 is connected through a switch 604 to a positive terminal of the charge pump 526. The negative terminal node 603 of the battery 602 defines the fixed reference ground. The negative terminal of the charge pump 526 is connected through a switch 606 to the reference ground (battery negative terminal) when the switch 606 is closed. The positive and negative terminals of the charge pump 526 are also connected to the power supply node 515 and floating ground node 517 (of FIG. 5) through switches 608 and 610, respectively.

During a charging operation, the switches 608 and 610 are open and the switches 604 and 606 are closed, while the charge pump 526 is charged to a desired energy level. During the charging operation, the negative terminal of the charge pump is connected to a fixed ground through the switch 606. Once the charge pump 526 achieves a desired energy charge level, the switches 604 and 606 are opened and the switches 608 and 610 are closed. When the switches 608 and 610 are closed, the charge pump 526 is connected through the nodes 615 and 617 across the power supply terminals 515 and 517 of CR circuit 502 (FIG. 5). When the switch 606 is opened and the switch 610 is closed, the charge pump 526 becomes a floating power supply in that the negative terminal thereof is no longer tied to a fixed ground level. Instead, the floating ground node 517, and the negative power supply terminal 517 of the charge pump 526, are allowed to float up and down in voltage (relative to a fixed ground). The charge pump 526 represents a "floating power supply" as a voltage at the negative terminal of the charge pump 526 (corresponding to the node 517) is permitted to drift, or otherwise fluctuate, upward and downward (relative to a reference ground) and is not tied to a fixed voltage reference (e.g., 0 V). As a further example, when a negative terminal of the battery defines the fixed reference ground, the negative terminal of the charge pump 526 is not directly electrically connected to, and is electrically separate from, the negative terminal of the battery (as switch 606 is open). As a further example, the term "floating power supply" shall mean a power supply, for which the negative terminal is not electrically connected to, and is electrically separate from, the negative terminal node 603 of the battery, but instead is allowed to drift upward and downward relative to the reference ground. As explained hereafter, during an EMI event, the floating ground node 517 is electrically separate from the negative terminal of the power supply (battery 602) in order that a voltage potential at the floating ground node 517 is able to drift relative to a voltage potential at the negative terminal node 603 to maintain a stimulation profile during delivery of the stimulation therapy while in the presence of the EMI event.

Returning to FIG. 5, the error amplifier 520 includes first and second input terminals (designated by the positive and negative signs). The first input terminal is connected to a digital analog converter (DAC) reference 529. The DAC reference 529 operates as a reference voltage source to supply a reference voltage signal at the first input (positive) terminal of the CR circuit 502. The DAC reference 529 is controlled by the microcontroller 314 (FIG. 3) to output a reference voltage that defines a stimulation profile of the stimulation therapy. A feedback line 531 is coupled to the second input (negative) input of the CR circuit 502 and a variable resistor 524 and provides a feedback signal indicative of a voltage potential at a source of a MOSFET transistor 522 (which is also indicative of the current pulled from the active electrode E1). The CR circuit 502 generates an output current based on the voltage across the variable resistor 524, which is controlled by the voltages at the first and second input terminals (positive and negative terminals) corresponding to the feedback signal 531 and the reference voltage from the DAC reference 529. The output of the error amplifier 520 is connected to, and drives, a gate of the MOSFET transistor 522. The transistor 522 includes a drain connected to the electrode E1 at node 521 and a source connected to the variable resistor 524 at the feedback node 512. The transistor 522 is configured to regulate the stimulation current flow through the electrode E1 based on the control voltage output by the error amplifier 520. The variable resistor 524 is connected between the feedback node 512 and the floating ground node 517.

During stimulation delivery, a current delivered to the patient is controlled by the CR circuit 502 based on a reference voltage supplied by the DAC reference 529. The DAC reference 529 is controlled by the microcontroller 314

(FIG. 3) to output a reference voltage that in turn drives the error amplifier 520 and transistor 522 to manage a level of current flow delivered at electrode E1 during each stimulation phase.

During delivery of stimulation, the electrode E1 exhibits a voltage $V_{cathode}$ with a stimulation current $i_{stim}$ flowing therethrough. The stimulation current $i_{stim}$ also flows through the electrode E2 which exhibits a voltage $V_{anode}$. The electrode E2 is connected to the voltage multiplier 534, thus the voltage $V_{anode}$ corresponds to the voltage $V_m$ across the voltage multiplier 534. While not illustrated, it is understood that the voltage multiplier 534 (FIG. 5) may be connected to the battery 602 through a set of switches similar to the configuration of switches 604-610 in FIG. 6. Accordingly, the voltage multiplier 534 may be charged by the battery 602 a desired voltage level and then disconnected from the battery 602 (and disconnected from a fixed ground) to allow the voltage multiplier 534 to function as a floating voltage multiplier, in which a voltage level at the negative terminal fluctuates up and down with the voltage level at the floating ground node 517.

The voltage multiplier 534, DAC reference 529, error amplifier 520, charge pump 526 and resistor 524 are all connected to the floating ground node 517 and thus area allowed to drift up and down by a similar amount as a voltage at the floating ground node 517 fluctuates relative to the fixed reference ground 541 (corresponding to the negative terminal of the battery) to maintain a stimulation profile while in the presence of the EMI event. When in a presence of an EMI event, the voltage at the floating ground node 517 is allowed to drift upward and downward in response to the interference, and based thereon voltages drift upward and downward by related amounts at the first and second electrodes ($V_{anode}$, $V_{cathode}$), the power supply terminals of the error amplifier 520 (nodes 515, 517), the feedback line 531 and the feedback node 512. By allowing the floating ground node 517 to drift upward and downward, such as when exposed to EMI interference, embodiments herein afford sufficient operating range (also referred to as "headroom") to avoid voltage "clamping" by the charge pump 526, error amplifier 520, DAC reference 529, voltage multiplier 534 and/or other components. By allowing the floating ground node 517 to drift upward and downward, such as when exposed to EMI interference, embodiments herein avoid the charge pump 526, error amplifier 520, DAC reference 529, voltage multiplier 534 and other components from reaching or exceeding an outer voltage of the normal operating range of such components and/or entering a clamping state.

The active electrode E2 is coupled to a voltage multiplier 534 which is used during a stimulation therapy phase, and which can also be used during discharge operation. During the therapy phase, in which stimulation is delivered to the patient, the voltage multiplier 534 delivers a multiplied voltage $V_M$. The $V_M$ voltage may be different during the therapy and discharge phases, and will vary between patients and between different types of therapies. The voltage multiplier 534 is selectively connected to the battery through a series of switches during charging operations (in a manner similar to the configuration described previously in connection with FIG. 6 for the charge pump 526).

In the example of FIG. 5, the IPG is exposed to EMI interference (e.g., such as during an MRI scan, and accordingly, the schematic diagram also models EMI interference at electrodes E0, E1, and E2. An interference source 510 is modeled as a voltage source that is introduced at the inactive electrode E0 when the inactive electrode E0 is exposed to EMI interference. Interference sources 532 and 533 are similarly modeled as voltage sources that are introduced at the active electrodes E1 and E2, when the active electrodes E1 and E2 are exposed to EMI. The magnitude of the voltage introduced by the interference sources 510, 532, 533 fluctuates over time in a substantially similar manner (although not identically) at the active and inactive electrodes E0, E1, E2.

The active and inactive electrodes E1, E2 and E0 exhibit certain similar capacitive and resistive characteristics while implanted in the patient tissue that are also modeled as shown in FIG. 5. The active electrode E1 exhibits a resistance 528 and a capacitance 530 (e.g., 3 µF). The active electrode E2 exhibits a resistance 527 and a capacitance 525 (e.g., 3 µF). The inactive electrode E0 (operating as an EMI antenna) exhibits a resistance 514 and a capacitance 523. In general, the electrodes E1, E2 and E0 are designed to have similar capacitive and resistive characteristics, such that resistances are substantially similar and the capacitances are substantially similar. Optionally, when a "dummy" wire is used as the EMI antenna, the wire may also be configured to have similar capacitive and resistive characteristics as the active electrodes E1, E2, such that resistances are substantially similar and the capacitances are substantially similar. While a separate dummy wire is not illustrated in FIG. 5, it is understood that the wire EMI antenna would be connected to the circuit of FIG. 5 at the CASE node (rather than the COMMON node, where electrodes E0, E1, and E2 connect to the human tissue), since the non-electrode dummy wire must not electrically conduct to human tissue. During stimulation, a stimulation current is delivered in the direction indicated by the arrows $i_{STIM}$ proximate the resistors 527 and 528 and capacitors 525 and 530. Substantially no current travels from the COMMON node to the inactive electrode E0 or to the Case of the IPG (as noted by the arrows labeled i=0) with proper control of the $V_{com}$ voltage source 539.

The CASE of the IPG is connected to a voltage source 539 that is generated from the battery of the IPG and is configured to maintain a common mode voltage $V_{com}$ at the CASE electrode, thereby maintaining a predetermined average voltage potential across the entire electrode network. The voltage source 539 includes a negative terminal that is connected to the negative terminal of the battery at the ground 541. The voltage source 539 adds the common mode voltage to the Case of the IPG, in order to raise the entire electrode network to the common mode voltage, which in turn offsets induced voltages introduced by EMI interference. Raising the electrode network to the common mode voltage prevents the EMI interference from interfering, through the Case electrode, with a performance of the circuitry 500 while operating in the presence of EMI events.

Optionally, the EMI antenna (e.g., inactive electrode E0 and/or wire) may be utilized to measure an amount of voltage induced by EMI interference. As noted herein, the EMI antenna (e.g, inactive electrode E0 and/or wire) may be utilized to provide an EMI feedback signal indicative of an amount of interference voltage experienced at the active electrodes E1 and E2. The EMI feedback signal at electrode E0 will move up and down based on the level of EMI interference. In connection there with, inactive electrode E0 is coupled to a comparator circuit 548 that is configured to monitor the interference voltages and determine when the interference voltage is moving up or down. The output of the comparator circuit 548 is coupled to a processor or state machine circuit 547 that is configured to adjust the voltage $V_{COM}$ at the voltage source 539 in a manner inversely related to the interference voltage experienced at the inactive electrode E0. As a further example, as the EMI interference introduces a positive interference voltage (e.g., 10 V) at the electrode E0, the comparator circuit 548 and processor or state machine circuit 547 cooperate to reduce the voltage $V_{com}$ generated by the voltage source 539 by a substantially equal and opposite amount (e.g., −10 V) to the interference voltage.

FIG. 5 also illustrates a DC blocking capacitor 523 that is modeled in series with the CASE electrode and a COMMON node 540. The DC blocking capacitor 523 is configured to prevent DC current flow through the Case. Diodes 541-545 are connected to the corresponding electrodes E2, E1, E0 and the Case, which provide electrical damage protection to the NS system from electrostatic discharge (ESD) and/or cardiac defibrillation. More specifically, the diode 541 is connected between the electrode E2 and a floating voltage (VFLOAT). The diode 542 is connected between the electrode E1 and the floating voltage (VFLOAT). The diode 543 is connected between the electrode E0 and the floating voltage (VFLOAT). The diodes 544-545 are connected between the CASE electrode, the negative battery terminal 541, and the floating voltage (VFLOAT).

As a nonlimiting example, assume during an EMI event that the $V_{com}$ common mode voltage reference 539 is maintained between +/−10 V. When no EMI interference is present, the voltages at $V_{com}$ and at the floating ground node 517 may be biased to approximately 0 V. When EMI interference is experienced in a conventional NS system, the EMI interference adds voltage interferences at the electrodes E1 and E2 that cause their voltages to fluctuate upward and downward (e.g., in a sinusoidal manner). The voltage interferences at electrodes E1 and E2 would also cause the voltage at the floating ground node 517 to similarly fluctuate upward and downward by an amount substantially corresponding to the voltage interference, if the $V_{com}$ voltage for the present NS system embodiment were held at a constant value. However, in a NS system formed in accordance with embodiments herein, the $V_{com}$ common mode voltage reference 539 can be adjusted in real time to substantially cancel out the voltage interference caused by EMI. That interference cancellation behavior will hold the unused electrode E0 and the active electrodes E1 and E2 substantially constant at the average $V_{com}$ voltage, which will prevent voltage excursions for other electrical nodes in the NS system from causing deleterious effects while maintaining safe and effective stimulation therapy for the patient during the presence of EMI.

Figure 7:
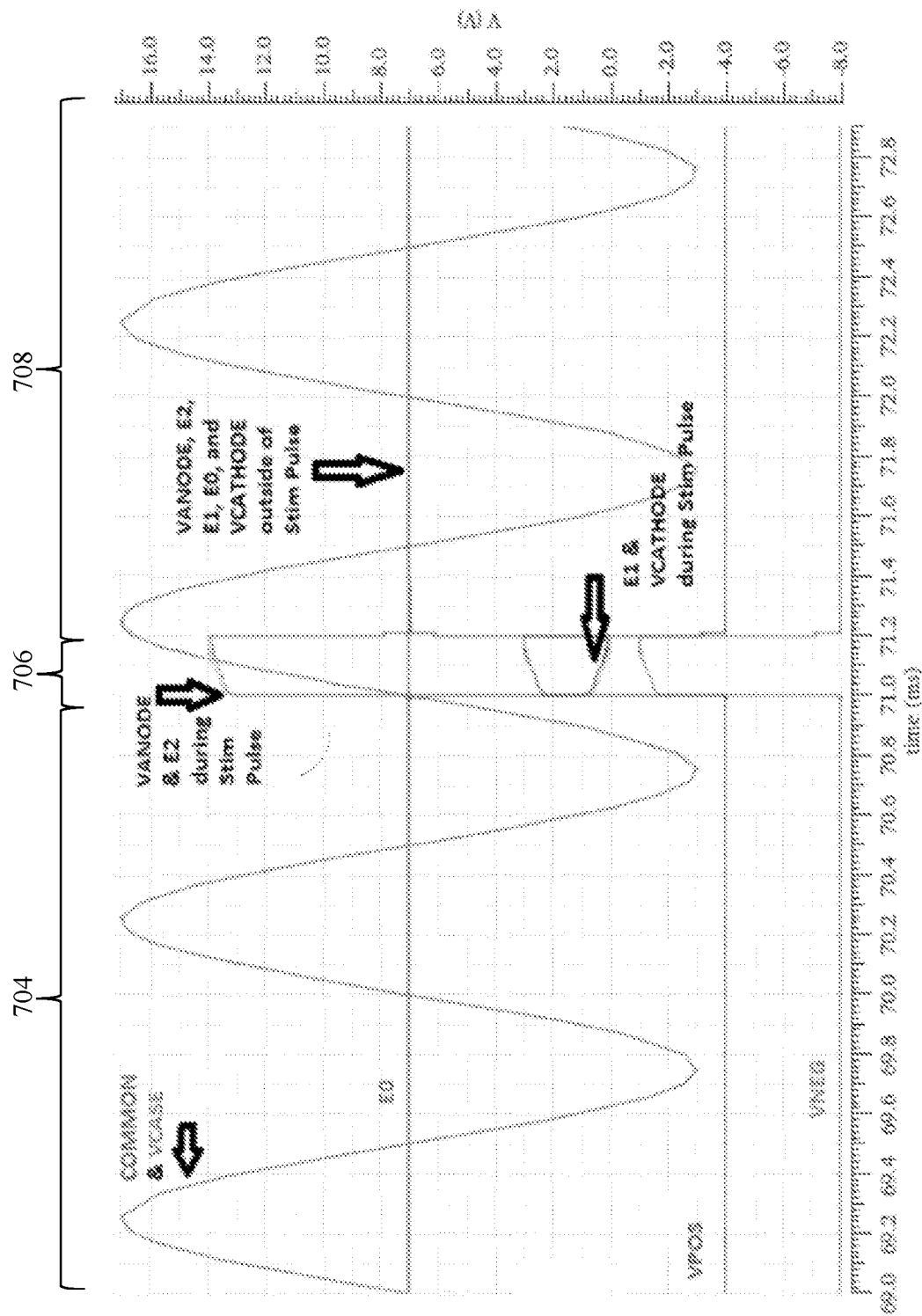
FIG. 7 illustrates an example of voltage potentials experienced at select points in an NS system before, during and after delivery of an NS therapy in the presence of EMI in accordance with embodiments herein.

FIG. 7 illustrates an example for voltage potentials experienced at select points in an NS system formed in accordance with embodiments herein before, during and after delivery of an NS therapy in the presence of EMI. By way of example, the timing diagram plots voltage along the vertical axis at various points within the NS system and time along the horizontal axis. In the timing diagram, the stimulation phase 706 corresponds to an interval in which a stimulation current pulse 702 is delivered to the active electrodes as part of an NS therapy, while the discharge phases 704 and 708 correspond to time periods before and after the stimulation current pulse 702 for dissipating charge which was built-up on the active electrodes during stimulation. During discharge phases 704 and 708, circuit nodes VANODE, E2, E1, and VCATHODE are substantially held at the average $V_{com}$ voltage, while nodes COMMON and Case are allowed to drift up and down to inversely track the interference voltage induced by the EMI. During stimulation phase 706, the voltages at VANODE and E2 are allowed to skew to above the average $V_{com}$ voltage, while in a substantially symmetric fashion the voltages at E1 and VCATHODE are allowed to skew below the average $V_{com}$ voltage. At all times, by use of control circuits (see circuits 547 and 548 in FIG. 5 and FIG. 8) which can monitor the amount of induced interference voltage on an unused electrode, the $V_{com}$ voltage can be adjusted in an inverse fashion to the induced interference and the voltage at unused electrode E0 is maintained substantially at the average $V_{com}$ voltage. This operation of the $V_{com}$ voltage ensures that optimal operating voltage "headroom" for the NS system is maintained during the EMI event for all components of the CR circuit 502 as well as all of the electrodes.

During stimulation therapy delivery, the NS system formed in accordance with embodiments herein maintains a high impedance electrical loop between the IPG case and the active stimulation electrode(s) at all times during a patient MRI scan and/or when subject to other types of EMI, to minimize stimulation interference and other concerns. By achieving a high impedance electrical loop behavior during both stimulation and discharge during an EMI event, the CR circuit is able to optimally manage NS system operation before, during and after stimulation while avoiding degradation of patient therapy from EMI. The CR circuit also mitigates patient safety concerns while allowing stimulation therapy to be continuously delivered during an MRI scan and/or in the presence of other EMI events. Other benefits of the embodiments herein include: 1) alleviating a need for a large amount of IPG memory, which would otherwise be necessary to store numerous digital parameters or values (e.g., the digital representation of the amplitude settings for the CR circuit) to control stimulation therapy and discharge currents; 2) alleviating a need for a complex digital state machine, which would otherwise be necessary to control the timing and reading of parameters for controlling the therapy and discharge currents; 3) alleviating a need for extracting a model for the IPG load, which would otherwise be necessary to determine the control parameters for therapy and discharge; 3) eliminating the effects of model errors which could introduce undesirable stimulation artifacts or could further degrade stimulation efficiency or efficacy; and 4) alleviating the need for an extensive number of calculations needed for computing the control parameters required for the CR circuit.

Figure 8:
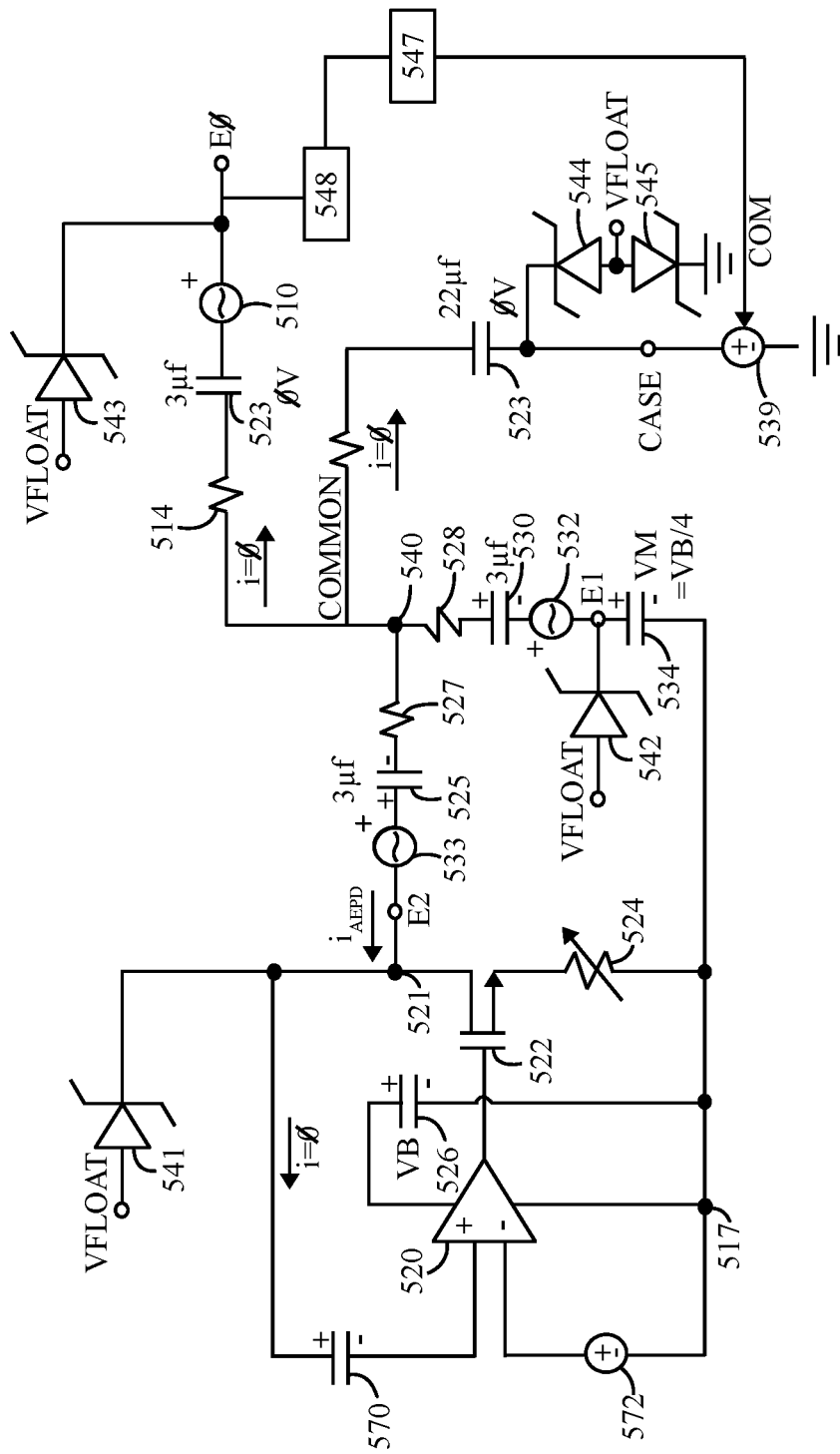
FIG. 8 illustrates a portion of the electrodes and circuitry in a NS system when operating in a discharge mode/configuration in accordance with embodiments herein.

FIG. 8 illustrates the NS system when operated in a discharge mode/configuration, in accordance with embodiments herein. Several of the components remain connected in the manner described above in accordance with FIG. 5. However, when in the discharge configuration, the first input terminal of the error amplifier 520 is connected to a voltage level shift component (e.g., capacitor) 570, while the second input terminal is connected to a reference voltage source 572. A negative terminal of the reference voltage source 572 is connected to the floating ground node 517. The voltage level shift component 570 is connected between the first input terminal and the node 521 associated with the electrode E2. The drain of the transistor 522 is connected to the node 521 associated with the electrode E2. The electrode E1 is connected to a positive terminal of a voltage multiplier 534. A negative terminal of the voltage multiplier 534 is connected to the floating ground node 517.

The discharge mode/configuration of FIG. 8 operates in a manner which actively emulates passive discharge (AEPD), such as for discharge in DBS applications that utilize an efficient and preferred Monopolar stimulation electrode configuration (i.e. use of the IPG Case/Can as the anode electrode). One advantage of the NS system embodiment described herein is that it helps to minimize the power consumption of the AEPD operation during MRI/EMI. Other NS system performance benefits of the AEPD functionality during MRI/EMI are described in further detail in U.S. patent application Ser. No. 16/401,943, titled "NEUROSTIMULATION METHOD AND SYSTEM FOR ACTIVE EMULATION OF PASSIVE DISCHARGE IN PRESENCE OF MRI/EMI INTERFERENCE".

Closing

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only and are thus not intended to limit in any way the definition and/or meaning of the term "controller circuit".

The computer, subsystem, controller circuit, and/or circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A neurostimulation (NS) system, comprising:
a power supply having positive and negative terminals, the negative terminal defining a reference ground;
an array of electrodes positioned within a patient, the array of electrodes including first and second active electrodes for delivering stimulation therapy configured to be located proximate to neural tissue that is associated with a target region;
a control circuit configured to control delivery of stimulation current for a NS therapy between the first and second electrodes;
a current regulator (CR) circuit connected to, and configured to control the stimulation current through, at least the first electrode during delivery of the stimulation therapy under direction of the control circuit; and
a floating power supply connected across power supply terminals of the CR circuit, the CR circuit and floating power supply coupled to a floating ground node that is electrically separate from the reference ground,
wherein, during delivery of the stimulation therapy and when in a presence of an EMI event, the voltage at the floating ground node drifts upward and downward in an inverse relation to the EMI event, and based thereon voltages drift upward and downward by related amounts at the first and second active electrodes to enable the CR circuit to maintain a stimulation profile.

2. A neurostimulation (NS) system, comprising:
a power supply having positive and negative terminals, the negative terminal defining a reference ground;
an array of electrodes positioned within a patient, the array of electrodes including first and second active electrodes for delivering stimulation therapy configured to be located proximate to neural tissue that is associated with a target region;
a control circuit configured to control delivery of stimulation current for a NS therapy between the first and second electrodes;
a current regulator (CR) circuit connected to, and configured to control the stimulation current through, at least the first electrode, during delivery of the stimulation therapy under direction of the control circuit; and
a floating power supply connected across power supply terminals of the CR circuit, the CR circuit and floating power supply coupled to a floating ground node that is electrically separate from the reference ground,
wherein, during delivery of the stimulation therapy and while in a presence of an EMI event, the floating ground node is electrically separate from the negative terminal of the power supply in order that a voltage potential at the floating ground node drifts relative to a voltage potential at the negative terminal to maintain a stimulation profile during delivery of the stimulation therapy while the presence of the EMI event to enable the CR circuit to maintain a stimulation profile.

3. The NS system of claim 1, wherein, during a discharge operation, the floating ground node is electrically separate from the negative terminal of the power supply in order that a voltage potential at the floating ground node and a voltage potential across the voltage supply terminals of the CR circuit maintain an actively emulated passive discharge (AEPD) profile during the discharge operation.

4. The NS system of claim 1, wherein the floating power supply includes a charge pump and a switch network, the switch network configured to connect the charge pump to the power supply when charging the charge pump, the charge pump configured to be disconnected from the power supply when powering the CR circuit during the EMI event.

5. The NS system of claim 1, further comprising a reference voltage source configured to supply a reference voltage as a first input to the CR circuit, the CR circuit having a second input to receive a feedback signal, the CR circuit configured to regulate the stimulation current flow through the first electrode based on the reference voltage and the feedback signal.

6. The NS system of claim 1, wherein the CR circuit comprises an error amplifier, and a transistor, the transistor configured to regulate the stimulation current through the first and second electrodes based on an output of the error amplifier to maintain the stimulation profile while in the presence of the EMI event.

7. The NS system of claim 1, further comprising an EMI antenna configured to sense and mitigate interference from the EMI event.

8. The NS system of claim 1, wherein the control circuit is configured to deliver the NS therapy continuously over successive therapy delivery intervals that are separated by corresponding successive discharge operations while in the presence of the EMI event.

9. The NS system of claim 1, wherein, when in a discharge configuration, a first input terminal of the CR circuit connects to a voltage level shift component, while a second input terminal is connected to a reference voltage source, a negative terminal of the reference voltage source connected to the floating ground node, the voltage level shift component connected between the first input terminal and the second electrode, the first electrode connected to a positive terminal of a voltage multiplier, a negative terminal of the voltage multiplier connected to the floating ground node.

10. A method for managing neurostimulation (NS), the method comprising:
providing an array of electrodes including first and second active electrodes for stimulation therapy delivery configured to be located proximate to neural tissue that is associated with a target region;
providing a power supply having positive and negative terminals, the negative terminal defining a reference ground;
during delivery of the stimulation therapy in a presence of an EMI event:
controlling delivery of a stimulation of an NS therapy during a therapy delivery interval between the first and second electrodes;
utilizing a current regulator (CR) circuit to control current flow through at least the first electrode during delivery of the stimulation therapy;
supplying power to the CR circuit from a floating power supply connected across power supply terminals of the CR circuit; and
coupling the CR circuit and floating power supply to a floating ground node that is electrically separate from the reference ground,
wherein, during delivery of the stimulation therapy and when in a presence of an EMI event, the voltage at the floating ground node drifts upward and downward in an inverse relation to an induced interference voltage caused by the EMI, and based thereon voltages drift upward and downward by related amounts at the first and second electrodes and the feedback signal to enable the CR circuit to maintain a stimulation profile.

11. The method of claim 10, wherein, during delivery of the stimulation therapy, a voltage potential at the floating ground node drifts relative to a voltage potential at the negative terminal to maintain the stimulation profile during delivery of the stimulation while in the presence of an EMI event.

12. The method of claim 10, wherein, during a discharge operation, maintaining the floating ground node electrically separate from the negative terminal of the power supply in order that a voltage potential at the floating ground node and a voltage potential across the power supply terminals of the CR circuit maintain an actively emulated passive discharge (AEPD) profile during the discharge operation.

13. The method of claim 10, further comprising providing the floating power supply with a charge pump, connecting the power supply to the charge pump when charging the charge pump and disconnecting the power supply from the charge pump when powering the CR circuit during the EMI event.

14. The method of claim 10, further comprising supplying a reference voltage as a first input to the CR circuit and supplying a feedback signal as a second input to the CR circuit, utilizing the CR circuit for regulating the stimulation current flow through the first electrode based on the reference voltage and feedback signal.

15. The method of claim 10, wherein the CR circuit comprises an error amplifier and a transistor, the transistor configured to regulate the current flow through the first and second electrodes based on an output of the error amplifier to maintain the stimulation profile while in the presence of the EMI event.

16. The method of claim 10, wherein, when in a discharge configuration, a first input terminal of the CR circuit connects to a voltage level shift component, while a second input terminal of the CR circuit is connected to a reference voltage source, a negative terminal of the reference voltage source connected to the floating ground node, the voltage level shift component connected between the first input terminal and the second electrode, the first electrode connected to a positive terminal of a voltage multiplier, a negative terminal of the voltage multiplier connected to the floating ground node.

17. The method of claim 10, further comprising providing an EMI antenna, utilized for sensing and mitigating the interference from the EMI event.

18. The method of claim 10, further comprising delivering the NS therapy continuously over successive therapy delivery intervals that are separated by corresponding successive discharge operations while in the presence of the EMI event.

* * * * *